(12) United States Patent
Truckey

(10) Patent No.: US 10,499,897 B2
(45) Date of Patent: Dec. 10, 2019

(54) DISTRACTOR WITH BIDIRECTIONAL RATCHET

(71) Applicant: Thompson Surgical Instruments, Inc., Traverse City, MI (US)

(72) Inventor: Adam Truckey, Suttons Bay, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 421 days.

(21) Appl. No.: 15/450,584

(22) Filed: Mar. 6, 2017

(65) Prior Publication Data

US 2018/0249992 A1 Sep. 6, 2018

(51) Int. Cl.
*A61B 17/02* (2006.01)
*A61B 17/00* (2006.01)

(52) U.S. Cl.
CPC ........ *A61B 17/025* (2013.01); *A61B 17/0206* (2013.01); *A61B 2017/00407* (2013.01); *A61B 2017/0256* (2013.01)

(58) Field of Classification Search
CPC .............. A61B 17/025; A61B 17/0206; A61B 2017/0256; A61B 2017/00407
See application file for complete search history.

(56) References Cited

U.S. PATENT DOCUMENTS

| | | |
|---|---|---|
| 4,957,495 A | 9/1990 | Kluger |
| 5,059,194 A | 10/1991 | Michelson |
| 5,219,349 A | 6/1993 | Krag et al. |
| 5,944,658 A | 8/1999 | Koros et al. |
| 6,139,493 A | 10/2000 | Koros et al. |
| 6,648,891 B2 | 11/2003 | Kim |
| D566,269 S | 4/2008 | Koros et al. |
| 7,494,463 B2 | 2/2009 | Nehls |
| 7,578,822 B2 | 8/2009 | Rezach et al. |
| 7,618,424 B2 | 11/2009 | Wilcox et al. |
| 8,100,828 B2 | 1/2012 | Frey et al. |
| 8,118,737 B2 | 2/2012 | Perez-Cruet et al. |
| 8,172,849 B2 | 5/2012 | Noon et al. |
| 8,192,440 B2 | 6/2012 | Jones et al. |
| 8,197,488 B2 | 6/2012 | Sorrenti et al. |
| 8,357,184 B2 | 1/2013 | Woolley et al. |
| 8,679,129 B2 | 3/2014 | Sorrenti et al. |
| 8,906,034 B2 | 12/2014 | Gleeson et al. |
| 9,060,757 B2 | 6/2015 | Lawson et al. |
| 9,101,413 B2 | 8/2015 | Masson et al. |
| 9,125,703 B2 | 9/2015 | McClintock et al. |
| 9,131,966 B2 | 9/2015 | Solitario, Jr. et al. |
| 9,179,947 B2 | 11/2015 | Bass |

(Continued)

*Primary Examiner* — Matthew J Lawson
(74) *Attorney, Agent, or Firm* — McAndrews, Held & Malloy, Ltd.

(57) ABSTRACT

A distractor system may include a distractor, a first distraction screw, and a second distraction screw. The first distraction screw includes a proximal end and a distal end having threads that affix the screw to bone. First and second arms are coupled to a crossbar via respective first and second ratchets and are configured to receive respective first and second distraction screws. The first ratchet includes a switch configured to select between ratcheted movement of the first arm along the crossbar toward the second arm and ratcheted movement of the first arm along the crossbar away from the second arm.

20 Claims, 6 Drawing Sheets

(56) References Cited

U.S. PATENT DOCUMENTS

| | | | |
|---|---|---|---|
| 2003/0055430 A1* | 3/2003 | Kim | A61B 17/0206 606/331 |
| 2005/0021040 A1 | 1/2005 | Bertagnoli | |
| 2005/0203533 A1 | 9/2005 | Ferguson et al. | |
| 2006/0247645 A1* | 11/2006 | Wilcox | A61B 17/025 606/86 R |
| 2007/0191856 A1 | 8/2007 | Gil et al. | |
| 2008/0077155 A1 | 3/2008 | Diederich et al. | |
| 2014/0031874 A1 | 1/2014 | Kucharzyk et al. | |
| 2014/0107656 A1* | 4/2014 | Masson | A61B 17/7077 606/90 |
| 2015/0238177 A1 | 8/2015 | Masson et al. | |
| 2016/0128737 A1 | 5/2016 | Coric et al. | |

\* cited by examiner

DISTRACTOR WITH BIDIRECTIONAL RATCHET

TECHNICAL FIELD

The present disclosure relates to a surgical devices, and more particularly to distractors that part adjacent vertebra.

BACKGROUND

Various surgical procedures involve the distraction of bones away from one another. For example, in a spinal discectomy, a distractor may temporarily part or separate the vertebrae that are adjacent the disc to be removed. In this manner, the distractor may provide sufficient separation between vertebrae to permit removal of the disc and subsequent introduction of an intervertebral implant.

Limitations and disadvantages of conventional and traditional approaches will become apparent to one of skill in the art, through comparison of such systems with the present disclosure as set forth in the remainder of the present application with reference to the drawings.

SUMMARY

Surgical devices, providing both distraction and compression of bone structures such as vertebral bodies, are substantially shown in and/or described in connection with at least one of the figures, and are set forth more completely in the claims.

Various advantages, aspects and novel features of the present disclosure, as well as details of various illustrated example supporting embodiments, will be more fully understood from the following description and drawings.

DETAILED DESCRIPTION

Figure 1:
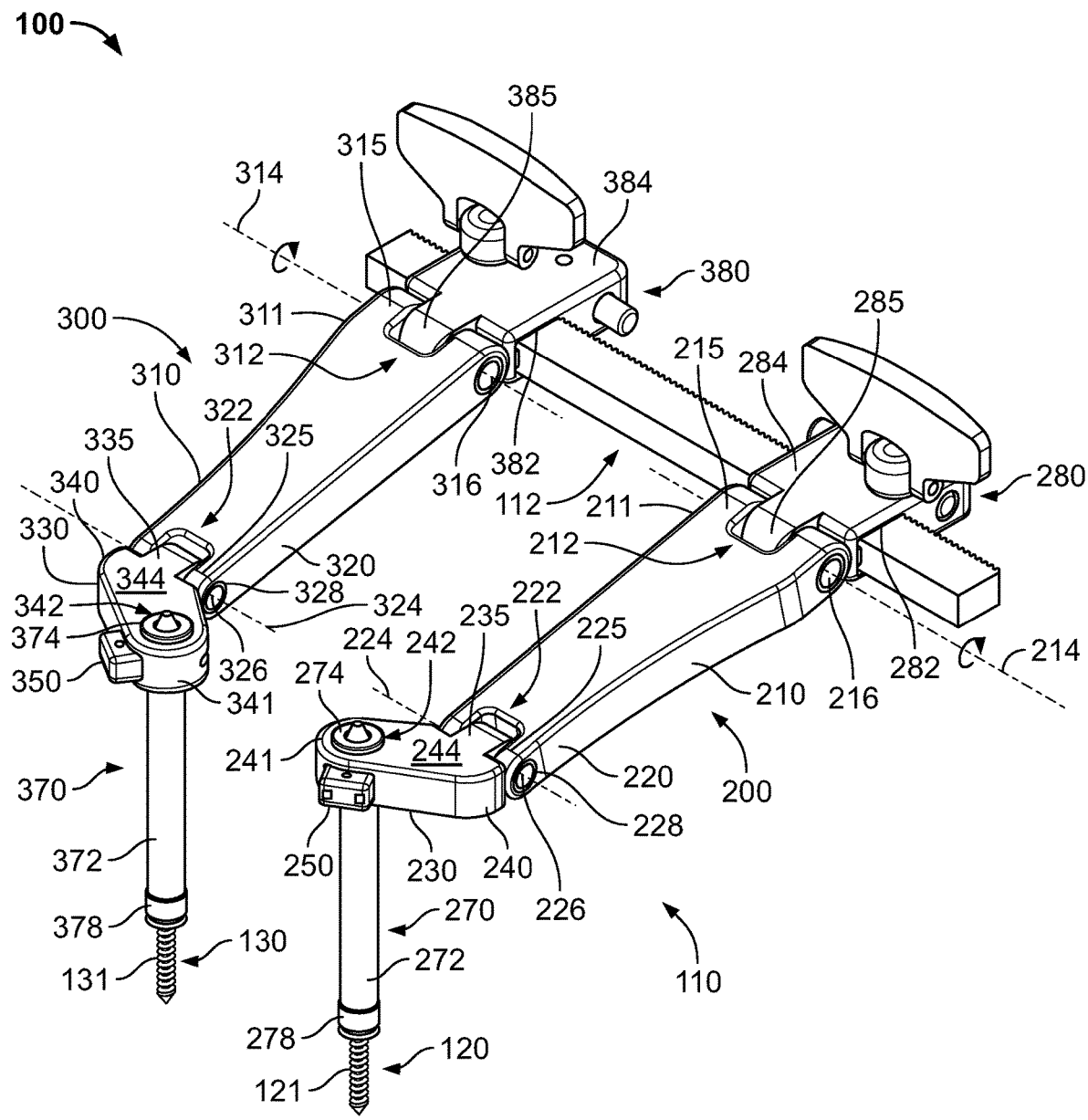
FIG. 1 provides a perspective view of a distractor system comprising a bidirectional distractor in accordance with an embodiment of the disclosure.

The following discussion presents various aspects of the present disclosure by way of one or more examples. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another element. Thus, for example, a first element, a first component or a first section discussed below could be termed a second element, a second component or a second section without departing from the teachings of the present disclosure. Similarly, various spatial terms, such as "upper," "lower," "side," and the like, may be used in distinguishing one element from another element in a relative manner. It should be understood, however, that components may be oriented in different manners, for example a component may be turned sideways so that its "top" surface is facing horizontally and its "side" surface is facing vertically, without departing from the teachings of the present disclosure.

In the drawings, various dimensions (e.g., layer thickness, width, etc.) may be exaggerated for illustrative clarity. Additionally, like reference numbers are utilized to refer to like elements through the discussions of various examples.

The discussion will now refer to various example illustrations provided to enhance the understanding of the various aspects of the present disclosure. It should be understood that the scope of this disclosure is not limited by the specific characteristics of the examples provided and discussed herein.

FIG. 1 provides a perspective view of an embodiment of a distractor system 100. The distractor system 100 may include an exemplary bidirectional distractor 110, a first distraction screw 120, and a second distraction screw 130. The bidirectional distractor 110 may include a crossbar 112, a first distractor arm 200, and a second distractor arm 300. The first distractor arm 200 may include a proximal arm portion 210, a distal arm portion 230, a lock 250, a screw sleeve 270, and a ratchet 280. Likewise, the second distractor arm 300 may include a proximal arm portion 310, a distal arm portion 330, a lock 350, a sleeve 370, and a ratchet 380.

In various embodiments, one or more parts of the distractor system 100 may be formed from surgical stainless steel. For example, bidirectional distractor 110 may be formed of 17-4 stainless steel, while distraction screws 120, 130 may be formed of 316 stainless steel. Other embodiments may utilize various alternative materials to form all or part of distraction system 100.

As shown, the screws 120, 130 may include threads 121, 131. The threads 121, 131 may enable driving or screwing the screws 120, 130 into bones. The threads may have a pitch between 1 mm and 2 mm to provide advancement of screws 120, 130 into bone by 1 mm to 2 mm per turn.

The distractor arms 200, 300 may be coupled to crossbar 112. As explained in greater detail below, the distractor arms 200, 300 may individually travel the crossbar 112. In particular, the first arm 200 may travel the crossbar 112 in a compression direction toward the second distractor arm 300 or may travel the crossbar 112 in a distraction direction away from the second distractor arm 300. Similarly, the second arm 300 may travel the crossbar 112 in a compression direction toward the first distractor arm 200 or may travel the crossbar 112 in a distraction direction away from the first distractor arm 200.

The crossbar 112 may pass entirely through a longitudinal aperture 282, 382 in a base portion 284, 384 of the ratchets 280, 380. As will be explained in greater detail below, the ratchets 280, 380 may impart both distraction and compression ratcheted-movement of the distractor arms 200, 300 along crossbar 112. Moreover, the ratchets 280, 380 may lock the distractor arms 200, 300 to crossbar 112 at locations along the crossbar 112 in order to maintain a desired distraction or compression force upon vertebral or other bodies affixed to screws 120, 130.

The distractor arms 200, 300 may each include multiple portions movably connected to one another. As shown, the distractor arms 200, 300 may each include a proximal arm portion 210, 310 and a distal arm portion 230, 330. Each proximal arm portion 210, 310 may include a proximal end 211, 311 pivotably coupled to the base portion 284, 384 of its respective ratchet 280, 380 via a hinge 212, 312.

Each hinge 212, 312 may be defined by one or more barrels 215, 315 of the proximal arm portion 210, 310, one or more barrels 285, 385 of the base portions 280, 380, and a pin 216, 316. The barrels 215, 315 may interleave with the barrels 285, 385 and define a longitudinal aperture 218, 318. Each pin 216, 316 may pass through the aperture 218, 318 defined by barrels 215, 285 and barrels 315, 385, thereby pivotally coupling distal ends 211, 311 of the proximal arm portions 210, 310 to respective base portions 280, 380.

As shown, each hinge 212, 312 may define a pivot axis 214, 314 about which the proximal arm portion 210, 310 may pivot. As shown, the hinges 212, 312 may provide pivot axes 214, 314 that are coplanar with and parallel to crossbar 112. In other embodiments, the hinges 212, 312 may orient pins 216, 316, barrels 215, 285, and barrels 315, 385 such that each axis 214, 314 is not coplanar with and/or is not parallel to cross bar 112. Furthermore, while each pivot axis 214, 314 is depicted as having the same orientation with respect to the crossbar 112, in some embodiments, the hinge 212 may orient the pivot axis 214 differently with respect to the crossbar 112 than the hinge 312 so as to provide pivot axes 214, 314 that are oriented differently from one another.

A proximal end 240, 340 of each distal arm portion 230, 330 may be pivotably coupled to a distal end 220, 320 of its respective proximal arm portion 210, 310 via a hinge 222, 322. Each hinge 222, 322 may be defined by one or more barrels 235, 335 of the distal arm portion 230, 330, one or more barrels 225, 325 of the proximal portions 210, 310, and a pin 226, 326. The barrels 225, 325 may interleave with the barrels 235, 335 and define a longitudinal aperture 228, 328. Each pin 226, 326 may pass through the aperture 228, 328 defined by barrels 225, 235 and barrels 325, 335, thereby pivotally coupling distal ends 220, 320 of the proximal arm portions 210, 310 to respective proximal ends 240, 340 of the distal arm portions 230, 330.

As shown, each hinge 222, 322 may define a pivot axis 224, 324 about which the distal arm portion 230, 330 may pivot. As shown, the hinges 222, 322 may provide pivot axes 224, 324 that are coplanar with and parallel to crossbar 112 and pivot axes 214, 314. In other embodiments, the hinges 222, 322 may orient pins 226, 326, barrels 225, 235, and barrels 325, 335 such that each axis 224, 324 is not coplanar with and/or is not parallel to cross bar 112 and/or pivot axes 214, 314. Furthermore, while each pivot axis 224, 324 is depicted as having the same orientation with respect to the crossbar 112, in some embodiments, the hinge 222 may orient the pivot axis 224 differently with respect to the crossbar 112 than the hinge 322 so as to provide pivot axes 224, 324 that are oriented differently from one another.

As shown, each distractor arm 110, 120 may further include a sleeve 270, 370 that is affixed to a distal end 241, 341 of its respective distal arm portion 230, 330. As shown, each sleeve 270, 370 may comprise tube 272, 372 having a flange 274, 374 at a proximal end 276, 376 of the tube 272, 372. Each tube 272, 372 may pass through a bore 242, 342 in the distal end 240, 340 of the respective distal arm portion 230, 330. In one embodiment, each bore 242, 342 runs perpendicular to an upper surface 244, 344 of the respective distal arm portion 230, 330. The flange 274, 374 may rest against and be affixed to the upper surface 244, 344, thereby securing the sleeve 270, 370 to the distal arm portion 230, 330. In some embodiments, an other circumference of the tube 272, 372 may be sized such that sleeve 270, 370 is pressure fit within the bore 242, 344, thereby further securing the sleeve 270, 370 to the distal arm portion 230, 330.

The hinges 212, 312 and the hinges 222, 322 may enable positioning the distal arm portions 230, 330 and the affixed sleeves 270, 370 in an advantageous direction without repositioning the entire bidirectional distractor 110. For example, distal arm portions 230, 330 may be rotated to point generally downward with respect to the remainder of bidirectional distractor 110. Such a configuration may, for example, be advantageous to access the vertebrae of a patient where the bidirectional distractor 110 is mounted above the patient. It will be apparent that various other configurations may be possible.

As will be explained in greater detail below, the distraction screws 120, 130 may be adapted for insertion into bone. The distraction screws 120, 130 may also be sized to be received by distal ends 278, 378 of tubes 272, 372. After inserting distraction screws 120, 130 into bone and into distal ends 278, 378 of tubes 272, 372, a surgeon may operate ratchets 280, 380 to move distractor arms 200, 300 toward (i.e., in a compression direction) or away (i.e., in a distraction direction) from one another, thereby moving the distraction screws 120, 130 and the bones to which distraction screws 120, 130 are anchored.

Other embodiments of the bidirectional distraction may include alternative distraction arms. For example, an alternative bidirectional distractor may replace one of the distractor arms 200, 300 with a stationary distractor arm that is coupled to the crossbar in a manner that prevents travel of the arm along the crossbar 112. Other embodiments of the bidirectional distractor 110 may include fewer or additional distractor arms. For example, an alternative embodiment may include three distractor arms or only one distractor arm. Various alternative embodiments may utilize fewer or additional portions for a distractor arm. For example, a distractor arm may include only one portion and no hinges.

Figure 2:
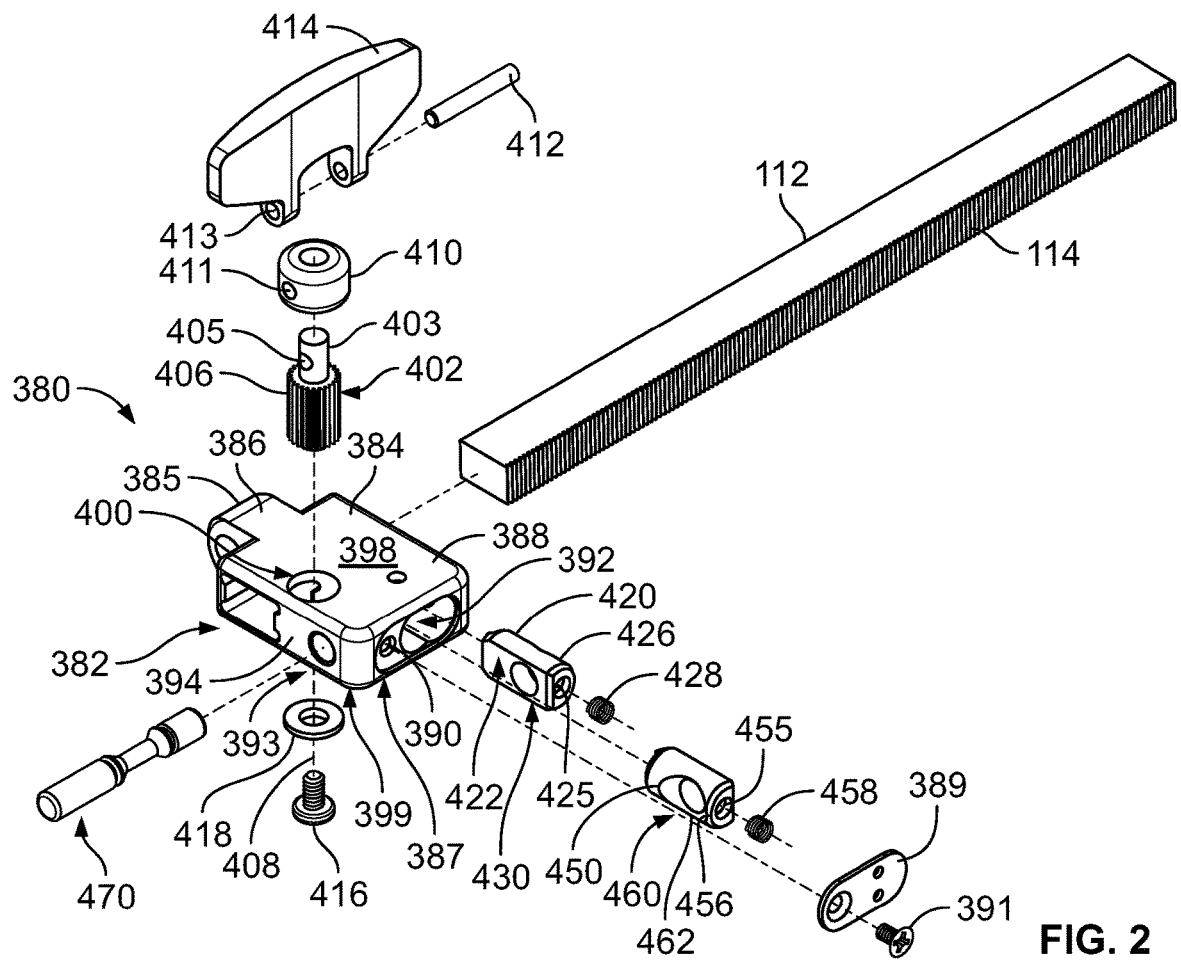
FIG. 2 provides an exploded view of a ratchet and crossbar of the bidirection distractor of FIG. 1.

FIG. 2 illustrates an exploded view of the ratchet 380 of the bidirectional distractor 110 in relation to the crossbar 112. The ratchet 280 may be implemented in a similar manner. As shown, the ratchet 380 includes the base portion 384 with longitudinal aperture 382 through which crossbar 112 passes. The base portion 384 may further include the one or more barrels 385 at a distal end 386. The base portion 384 may further include a recess 387 in a proximal end 388. The recess 387 may be sized to receive a base plate 389 and include a threaded bore 390 configured to receive a threaded screw 391 used to affix the base plate 389 in the recess 387.

As shown, the base portion 384 may further include an aperture 392 that passes through recess 387. The aperture 392 is sized to receive pawls 420, 450. In particular, internal sidewalls 393 mate with longitudinal sidewalls 422, 452 of the pawls 420, 450 and provide a passage 394, 395 along which each of the pawls 420, 450 may traverse. In particular, the passages 394, 395 may constrain movement of the pawls 422, 452 to movement toward the distal end 386 and crossbar teeth 114 and movement toward the proximal end 388 and away from crossbar teeth 114.

As shown, each of the pawls 420, 450 may include a recess 425, 455 in a proximal end 426, 456. Each recess 425, 455 may be sized to receive a respective spring 428, 458. When affixed in the recess 387, the base plate 389 may compress the springs 428, 458 thus causing the springs to provide a spring force that biases respective pawls 420, 450 toward the distal end 386 of base portion 384 and crossbar teeth 114.

The base portion 384 may further include a switch aperture 393 that passes laterally through sidewalls 394 of the base portion 384. Similarly, each of the pawls 420, 450 may include a switch aperture 430, 460 that passes laterally through sidewalls 422, 452 of the pawls 420, 450. When assembled, the switch apertures 393, 430, 460 may align so as to permit a switch 470 to pass through the base portion 384 and the pawls 420, 450. As explained in greater detail below, the switch 470 may slide along the apertures 393, 430, 460 and control which pawls 420, 450 engage crossbar teeth 114.

Furthermore, the base portion 384 may further include an adjustment aperture 400 that passes through an upper surface 398 and a lower surface 399. The adjustment aperture 400 may be sized to receive a pinion 402 of an adjustment device 404. The pinion 402 may include teeth 406 that extend radially from the pinion 402 and are sized to engage crossbar teeth 114. The pinion 402 may rotate about axis 408 which is parallel to the side of the crossbar 112 having teeth 114.

The adjustment device 404 may include a retaining collar 410 configured to receive a central axel 403 of pinion 402. The retaining collar 410 may have an outer circumference that is larger the outer circumference of the pinion 402 and adjustment aperture 400. The retaining collar 410 and axel 403 may further include a bore 411, 405. A retaining pin 412 may pass through a bore 413 of an adjustment handle 414 and the bores 411, 405 in order to pivotally attach the handle 414 to the pinion 402. Furthermore, a screw 416 and washer 418 having a greater circumference than the adjustment aperture 400 may be affixed to pinion 402. In this manner the pinion 402 may be retained within the base portion 384 such that rotation of the handle 414 may translate into rotation of the pinion 402 and its teeth 406.

In particular, the pinion 402 may be manually turned counter-clockwise to cause the ratchet 380 and respective arm 300 to travel along crossbar 112 in a first direction (e.g., a distraction direction). The pinion 402 may also be manually turned clockwise to cause the ratchet 380 and respective arm 300 to travel along crossbar 112 in an opposite, second direction (e.g., a compression direction). Such motion may be impeded, however, by engaged pawls 420, 450 of the ratchet 380.

Figure 3:
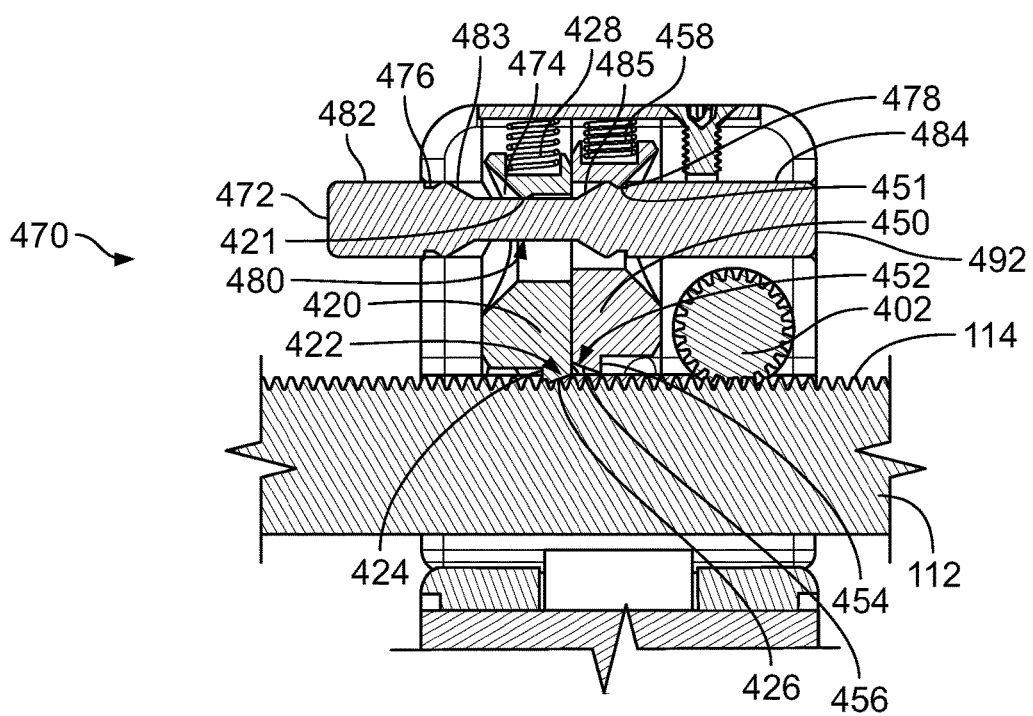
FIG. 3 provides a cross-sectional view of a ratchet having a switch position that permits travel along the crossbar in a first direction (e.g., a distraction direction).
Figure 4:
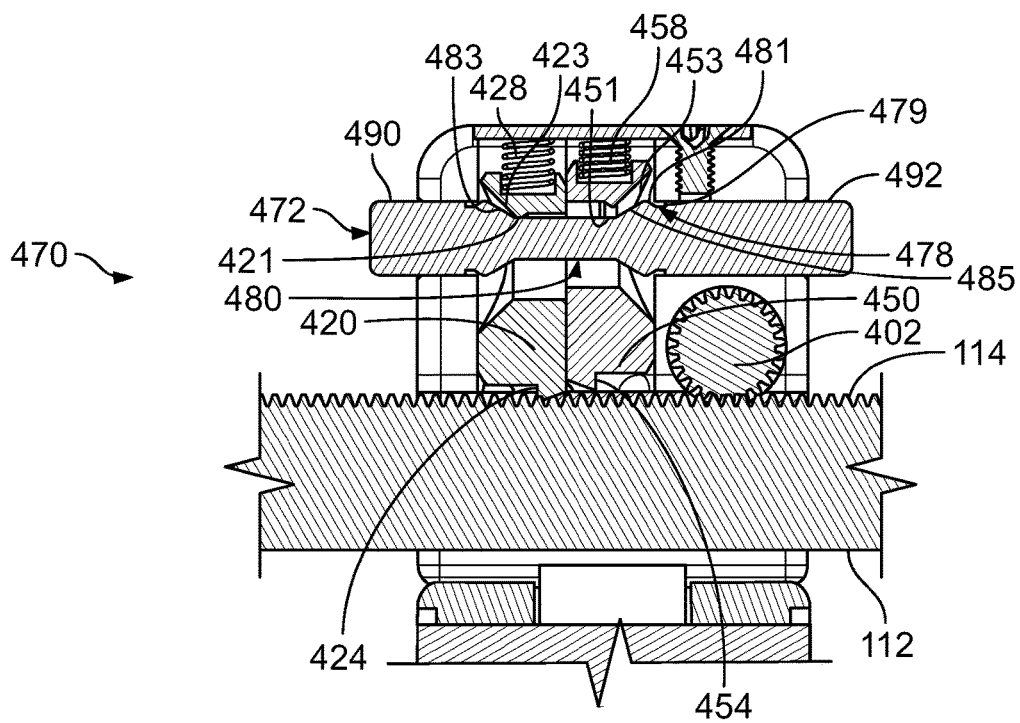
FIG. 4 provides a cross-sectional view of a ratchet having a switch position that does not permit travel along the crossbar.
Figure 5:
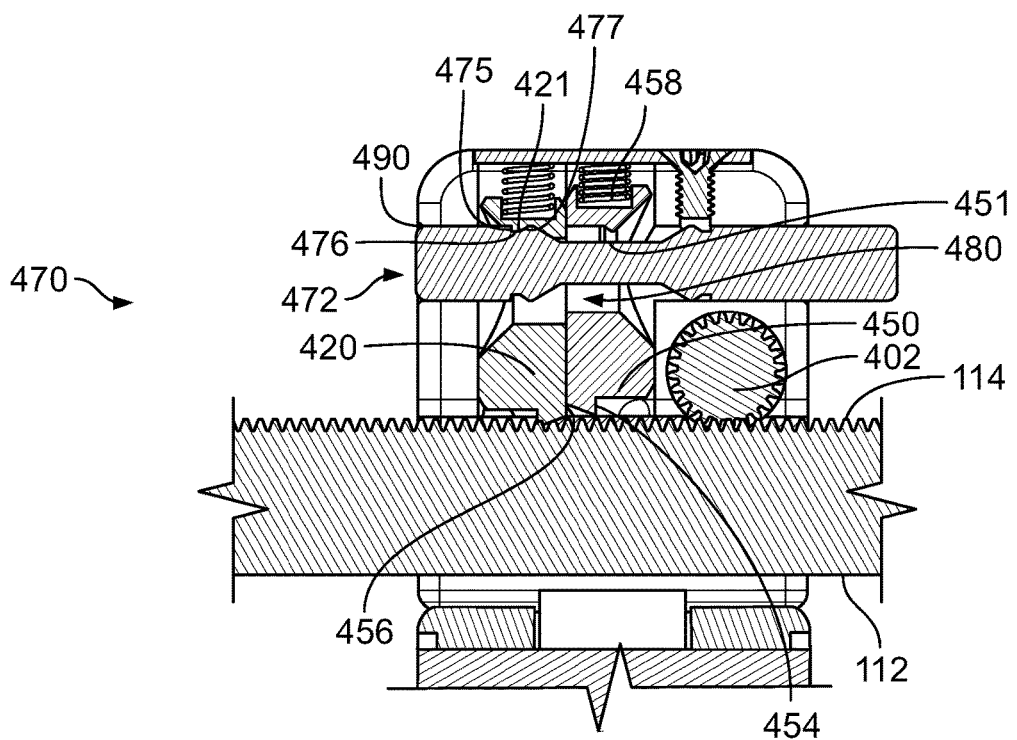
FIG. 5 provides a cross-sectional view of a ratchet having switch position that permits travel along the crossbar in a second direction (e.g., a compression direction).
Figure 6:
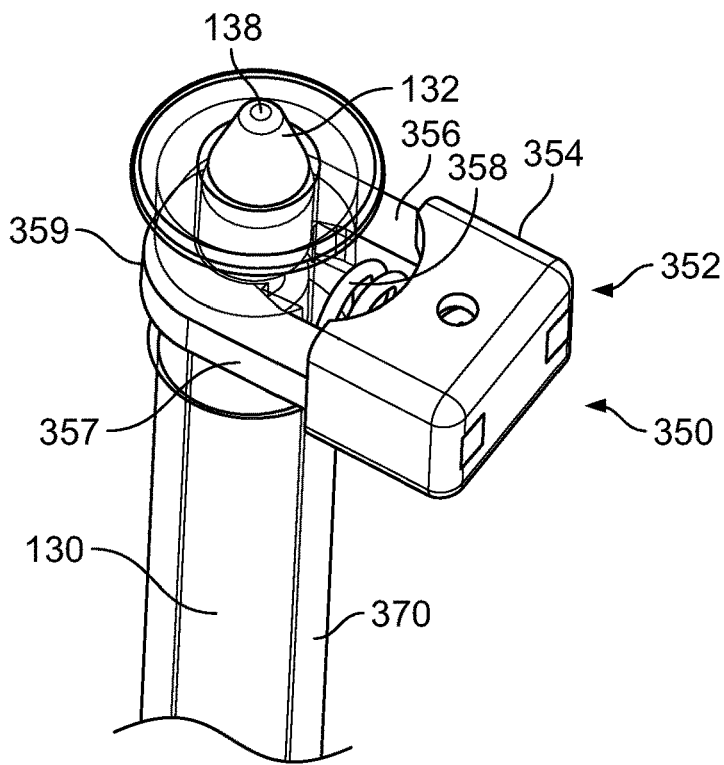
FIGS. 6 and 7 provide perspective views of a lock used to lock a distraction screw to the bidirectional distractor of FIG. 1.

Referring now to cross-sectional views of FIGS. 3-5, further details regarding the interaction between the switch 470 and the pawls 420, 450 are explained. In general, the switch 470 may selectively engage the pawls 420, 450 with the crossbar teeth 114 and thereby selectively inhibit movement of the arm 300 along the crossbar 112.

The pawl 420 may include a finger 422 that is sized to fit between adjacent crossbar teeth 114. A left edge 424 of the finger 422 may be steeply-sloped (e.g., perpendicular) with respect to the crossbar teeth 114 whereas the right edge 426 of the finger 422 may be gradually-sloped with respect to the crossbar teeth 114. When engaged, a biasing spring 428 urges the finger 422 against the crossbar teeth 114. The engaged, steeply-sloped left edge 424 prevents the ratchet 380 and arm 300 from traveling toward the steeply-sloped left edge 424 since the steep slope prevents lateral movement of the ratchet 380 from abruptly overcoming the biasing force applied to the pawl 420. Conversely, the engaged, gradually-sloped right edge 426 permits the ratchet 380 and arm 300 to travel toward the gradually-sloped ridge edge 426 since the gradual slope permits lateral movement of the ratchet 380 to gradually overcome the biasing force applied to the pawl 420.

The pawl 450 may include a finger 452 that is sized to fit between adjacent crossbar teeth 114. A right edge 454 of the finger 452 may be steeply-sloped (e.g., perpendicular) with respect to the crossbar teeth 114 whereas the left edge 456 of the finger 452 may be gradually-sloped with respect to the crossbar teeth 114. When engaged, a biasing spring 458 urges the finger 452 against the crossbar teeth 114. The engaged, steeply-sloped right edge 454 prevents the ratchet 380 and arm 300 from traveling toward the steeply-sloped right edge 454 since the steep slope prevents lateral movement of the ratchet 380 from abruptly overcoming the biasing force applied to the pawl 450. Conversely, the engaged, gradually-sloped left edge 456 permits the ratchet 380 and arm 300 to travel toward the gradually-sloped left edge 456 since the gradual slope permits lateral movement of the ratchet 380 to gradually overcome the biasing force applied to the pawl 450.

FIG. 3 depicts a position of the switch 470 that engages the pawl 420 with the crossbar teeth 114 and disengages the pawl 450 from the crossbar teeth 114. In such a position, the engaged pawl 420 permits movement toward its gradually-sloped right edge 426. Conversely, the engaged pawl 420 prevents movement toward its steeply-sloped left edge 424. Thus, FIG. 3 depicts a configuration of the switch 470 that permits movement of the ratchet 380 and its respective arm 300 in a first direction (e.g. a distraction direction) but prevents movement in an opposite direction (e.g., a compression direction).

To this end, the switch 470 may generally comprise a longitudinal, circular rod 472 that includes a central tapered portion 474, a first stop 476, and a second stop 478. The tapered portion 474 may comprise a central portion 480 having smaller diameter than an first end portion 482 and an opposite, second end portion 484. The tapered portion 474 may further include a first tapered surface 483 in which the diameter of the rod 472 gradually increases from the central portion 480 toward the first end portion 482. Similarly, the tapered portion 474 may further include a second tapered surface 485 in which the diameter of the rod 472 gradually increases from the central portion 480 toward the second end portion 484. Finally, the first stop 476 may comprise an annular groove around the first end portion 482 that is sized to receive a detent 421 of the pawl 420. Similarly, the second stop 478 may comprise an annular groove around the second end portion 484 that is sized to receive a detent 451 of the pawl 450.

As shown in FIG. 3, the switch 470 may be positioned such that the detent 421 and bore 430 of the pawl 420 align with the central portion 480 of the rod 472. In such a position, the biasing spring 428 may force the pawl 420 toward the crossbar teeth 114. In particular, the central portion 480 due to its smaller circumference may receive the detent 421 and thus permit the biasing spring 428 to move the pawl 420 into engagement with the crossbar teeth 114.

In the position of FIG. 3, the second stop 478 is aligned with the detent 451 of pawl 450. As shown in FIG. 4, the right side 479 of stop 478 is steeply-sloped whereas the left side 481 is gradually sloped. The steeply-sloped side 479 may prevent or stop the detent 451 from sliding past. As such, the detent 451 and steeply-sloped side 479 may prevent the switch 470 from sliding further to the left in FIG. 3. In one embodiment, the rod 472 may be sized and the stop 478 may be placed such that a right end 492 of the rod 472 is flush with an outer surface of the ratchet 480 when the switch 470 may be pushed no further to the left as shown in FIG. 3.

FIG. 4 depicts a position of the switch 470 that engages the pawl 420 and the pawl 450 with the crossbar teeth 114. In such a position, the engaged pawl 420 prevents movement toward its steeply-sloped left edge 424. Similarly, the engaged pawl 450 prevents movement toward its steeply-sloped right edge 454. Thus, FIG. 4 depicts a configuration of the switch 470 that effectively locks the ratchet 380 and its respective arm 300 in place.

As shown in FIG. 4, the switch 470 may be positioned such that the detents 421, 451 of the pawls 420, 450 align with the central portion 480 of the rod 472. In such a position, the biasing springs 428, 458 may force the respective pawls 420, 450 toward the crossbar teeth 114. In particular, the central portion 480 due to its smaller circumference may receive the detents 421, 451 and thus permit the biasing springs 428, 458 to move the pawls 420, 450 into engagement with the crossbar teeth 114.

From the position of FIG. 4, a user may push a left end 490 of the switch 470 toward the right to obtain the switch position shown in FIG. 5 or may push the right end 492 of the switch 470 toward the left to obtain the switch position shown in FIG. 3. When a user pushes the right end 492 toward the left, a gradually-sloped end surface 453 of the pawl 450 may engage and slide up the second tapered surface 485 of the rod 472. In this manner, the surfaces 453, 485 may translate force applied to the right end 492 to the pawl 450 in such a manner that overcomes the biasing force provided by spring 458 and moves the pawl 450 away from crossbar teeth 114. Conversely, when a user pushes the left end 490 toward the right, a gradually-sloped end surface 423 of the pawl 420 may engage and slide up the first tapered surface 483 of the rod 472. In this manner, the surfaces 423, 483 may translate force applied to the left end 490 to the pawl 420 in such a manner that overcomes the biasing force provided by spring 428 and moves the pawl 420 away from crossbar teeth 114.

FIG. 5 depicts a position of the switch 470 that disengages the pawl 420 from the crossbar teeth 114 and engages the pawl 450 to the crossbar teeth 114. In such a position, the engaged pawl 450 permits movement toward its gradually-sloped left edge 456. Conversely, the engaged pawl 420 prevents movement toward its steeply-sloped right edge 454. Thus, FIG. 5 depicts a configuration of the switch 470 that permits movement of the ratchet 380 and its respective arm 300 in a second direction (e.g. a compression direction) but prevents movement in an opposite direction (e.g., a distraction direction).

As shown in FIG. 5, the switch 470 may be positioned such that the detent 451 of the pawl 450 align with the central portion 480 of the rod 472. In such a position, the biasing spring 458 may force the pawl 450 toward the crossbar teeth 114. In particular, the central portion 480 due to its smaller circumference may receive the detent 451 and thus permit the biasing spring 458 to move the pawl 450 into engagement with the crossbar teeth 114.

In the position of FIG. 5, the first stop 476 is aligned with the detent 421 of pawl 420. As shown, the left side 475 of the stop 476 is steeply-sloped whereas the right side 477 is gradually sloped. The steeply-sloped side 475 may prevent or stop the detent 421 from sliding past. As such, the detent 421 and steeply-sloped side 475 may prevent the switch 470 from sliding further to the right in FIG. 5. In one embodiment, the rod 472 may be sized and the stop 476 may be placed such that a left end 490 of the rod 472 is flush with an outer surface of the ratchet 480 when the switch 470 may be pushed no further to the right as shown in FIG. 5.

Figure 7:
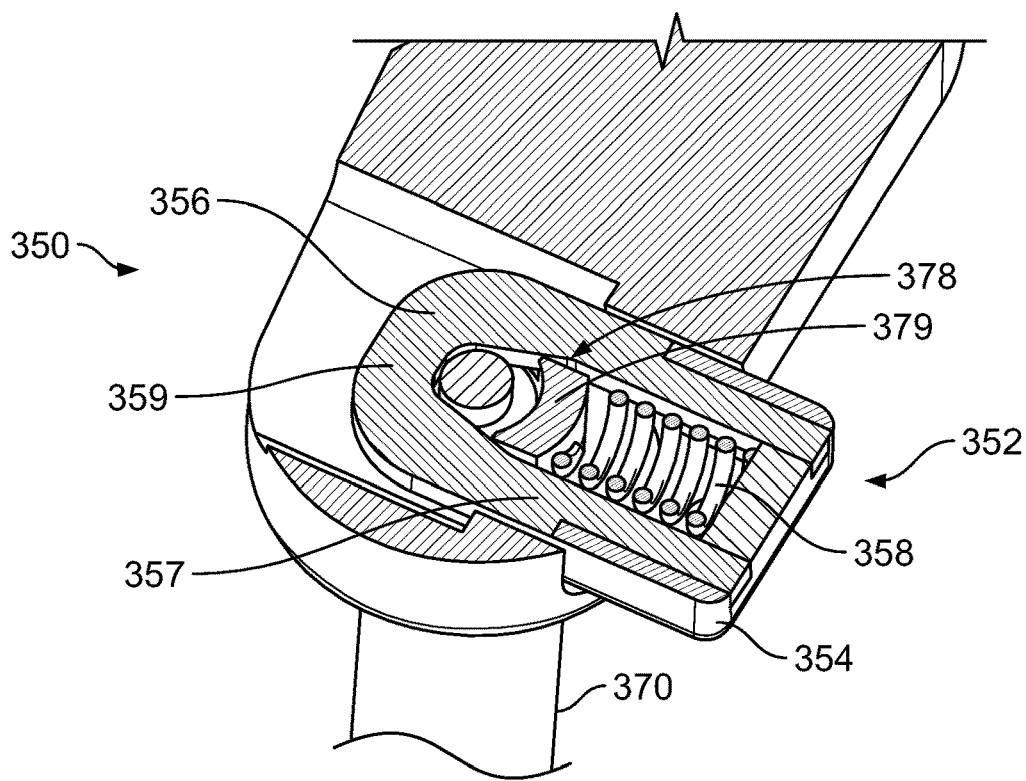

Referring now to FIGS. 6-11, details regarding the lock 350 and its interaction with the distraction screw 130 are illustrated. The lock 250 may be implemented to interact with the distraction screw 120 in a similar manner. As illustrated, the sleeve 370 may include an interior bore 376 and a slot 378 that accommodates and receives a key 352 of the lock 350. As best illustrated in FIG. 7, the slot 378 nearly circumscribes the sleeve 370, but for a portion 379 that maintains a connection between upper and lower portions of the sleeve 370. As further illustrated, the key 352 may include a button 354, stem 356, and a spring 358.

The interior bore 376 may have an internal circumference that is slightly larger than the external circumference of the distraction screw 130. In this manner, the interior bore 376 may receive and closely mate with the distraction screw 130. Further, a distal end 332 of the distal arm portion 330 may include a slot 334 that extends through the exterior of distal arm portion 330 and aligns with the slot 378 in the sleeve 370. In various embodiments, the slot 334 may extend from one exterior surface of the distal arm portion 330, through the interior bore 376, to the opposite exterior surface of the distal arm portion 330. The slot 334 may be sized to receive the stem 356 of the key 352. The stem 356 may have a U-shaped comprising to two adjoining arms 357. The arms 357 may be inserted into the end of the slot 334 opposite the retaining portion 379 of the sleeve 370. The arms 357 may extend to either side of the retaining portion 379, thus capturing the retaining portion 379 within the stem 356. The spring 358 may be placed between the retaining portion 379 and the button 354 before the button 354 is affixed to the arms 357. In this manner, the key 352 circumscribes the retaining portion 357 and is retained in the slot 334 of the distal arm portion 330. The key 352 may be slidable within the slot 334 between an open and a closed position. The spring 358 may be a compression spring and may bias the key 352 such that the button 354 is urged outwardly toward the closed position.

FIGS. 8-11 illustrate an interaction between an upper portion 132 of the distraction screw 130 and the lock 350. The distraction screw 120 may interact with the lock 250 in a similar manner. As shown, the distraction screw 130 may include a locking groove 134 and a tapered portion 136. The locking groove 134 may be configured to be engaged by the stem 356 of the lock 350. As illustrated, locking groove 134 may having a substantially square profile and may circumscribe the upper portion 132 of the screw 130. In particular, the locking groove 134 may be sized to receive the arms 357 and adjoining portion 359 of the stem 354.

Figure 8:
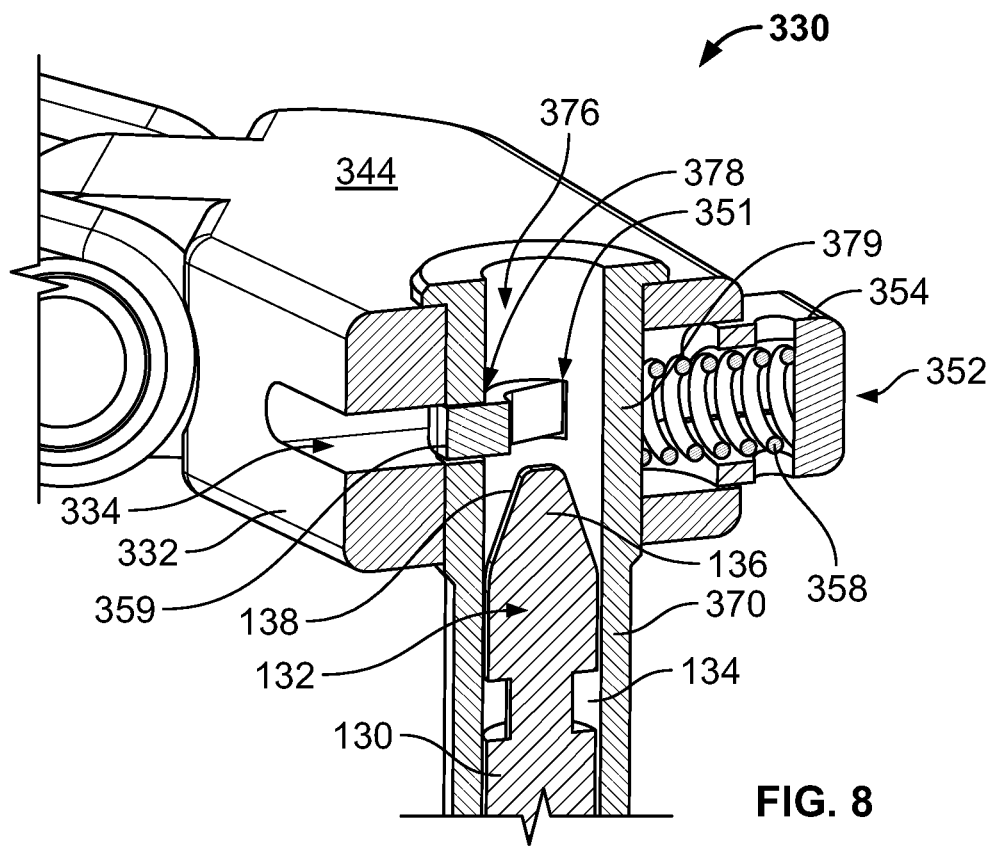
FIGS. 8-11 provide cross-sectional views depicting an interaction of the lock of FIGS. 6 and 7 with an upper portion of a distractor screw.

As further illustrated, the tapered portion 136 of the screw 130 may engage the stem 354 of the lock 350 as the screw 130 is inserted. In particular, FIG. 8 depicts the lock 350 in its biased closed or locked position. As shown, the retaining portion 379 is nearly as wide as the diameter of the circular adjoining portion 359 of the stem 356. As such, the adjoining portion 359 retains a gap 351 between the adjoining portion 359 and the retaining portion 379. The tapered portion 136 is angled or tapered such that the upper end 138 of the screw 130 is received by the gap 351 as the screw is inserted into the lock 350.

Figure 9:
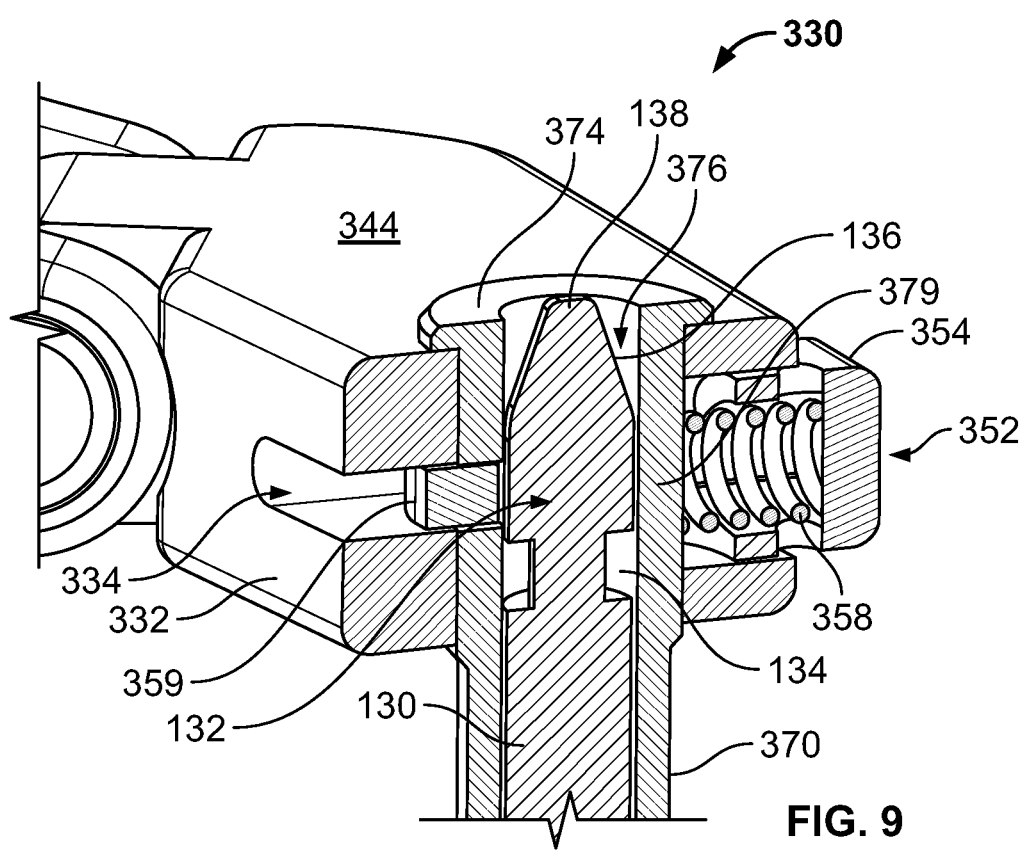
Figure 10:
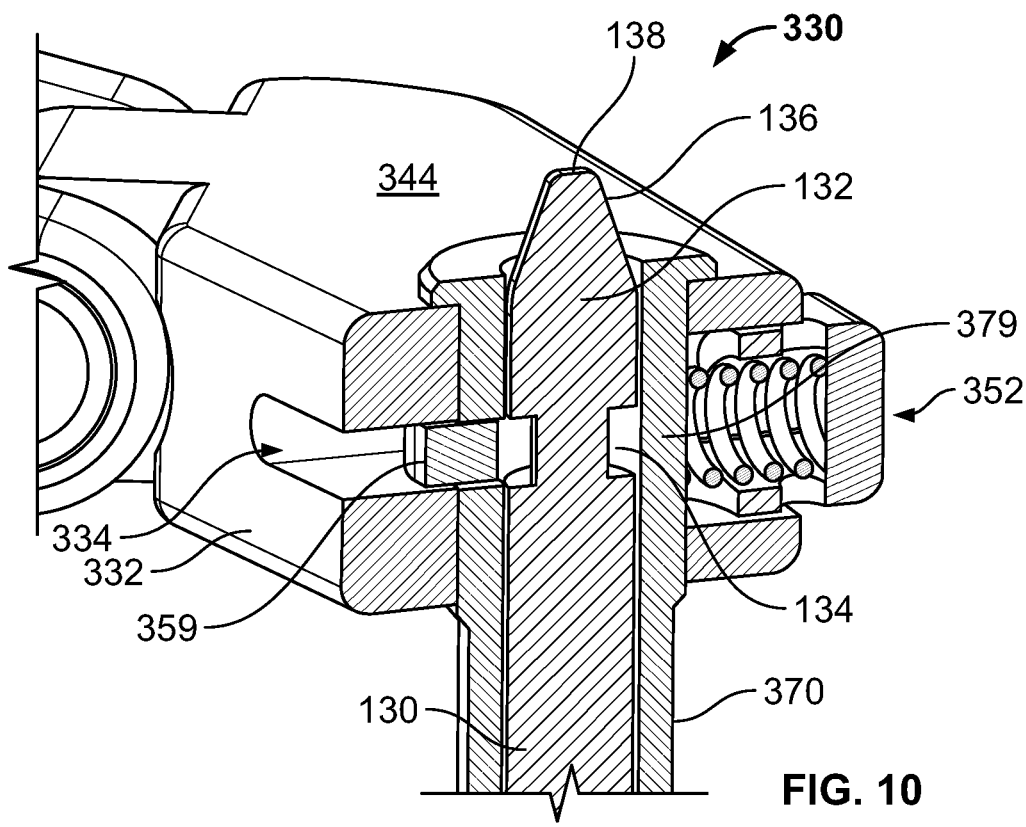
Figure 11:
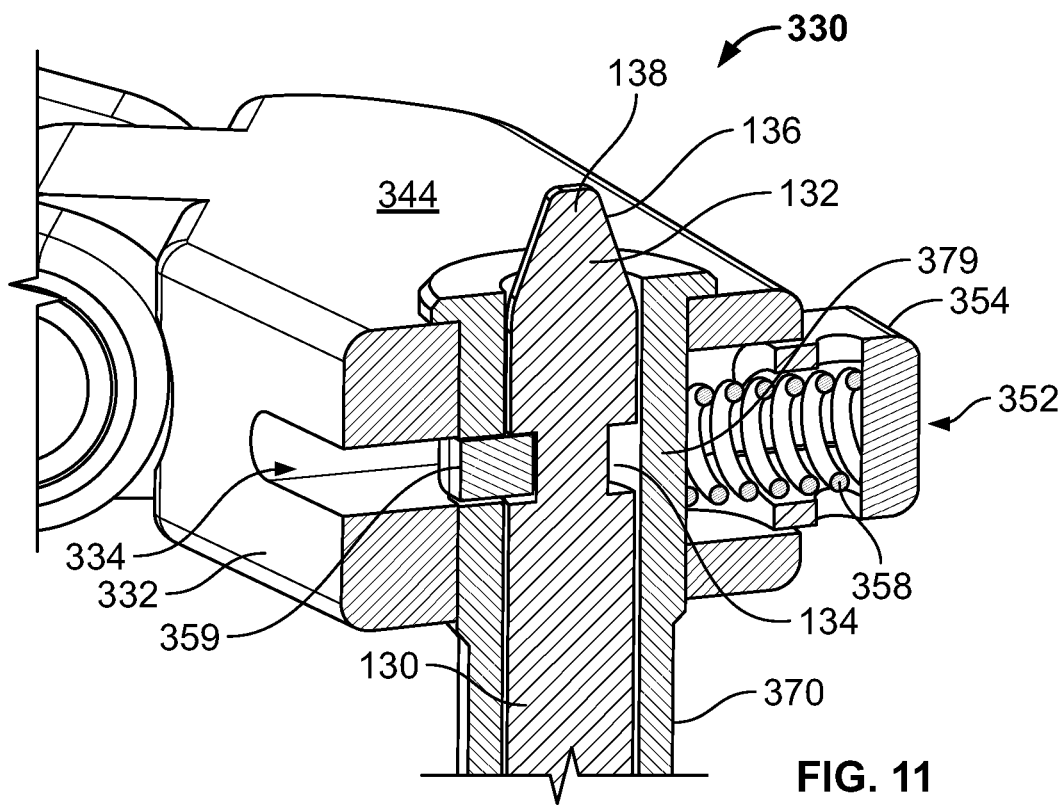

As shown in FIG. 9, the angled surfaces provided by the tapered portion 136 engage the adjoining portion 359 and urge the stem 356 and button 354 toward an open position as the screw 130 continues to travel toward a locked position. FIG. 10 depicts the locking groove 134 of the screw 130 aligned with the adjoining portion 359 of the stem 354. Once the locking groove 134 aligns with the stem 354, the biasing spring 358 urges the stem 354 and button 352 back to the locked position. In particular, the biasing spring 358 may abruptly cause the stem 354 to engage the locking groove 134 or audibly snap into place as shown in FIG. 11. In order to release the screw, the button 354 may be pressed and held to achieve the open position as shown in FIG. 10. The screw 130 may then be successively withdrawn in a manner shown in FIG. 9 and FIG. 8.

While the foregoing has been described with reference to certain aspects and examples, it will be understood by those skilled in the art that various changes may be made and equivalents may be substituted without departing from the scope of the disclosure. In addition, many modifications may be made to adapt a particular situation or material to the teachings of the disclosure without departing from its scope. Therefore, it is intended that the disclosure not be limited to the particular example(s) disclosed, but that the disclosure will include all examples falling within the scope of the appended claims.

What is claimed is:

1. A distractor for use with a first distraction screw and a second distraction screw, the distractor comprising:
    a crossbar comprising teeth;
    a first arm comprising a proximal end coupled to the crossbar and a distal end configured to receive the first distraction screw;
    a second arm comprising a proximal end coupled to the crossbar via a bidirectional ratchet and a distal end configured to receive the second distraction screw;
    wherein the bidirectional ratchet comprises a switch configured to selectively control ratcheted movement of the second arm along the crossbar;
    wherein the switch, when in a first switch position, configures the bidirectional ratchet to permit movement of the second arm along the crossbar in a first direction toward the first arm and configures the bidirectional ratchet to prevent movement of the second arm along the crossbar in a second direction away from the first arm;
    wherein the switch, when in a second switch position, configures the bidirectional ratchet to permit movement of the second arm along the crossbar in the second direction and configures the bidirectional ratchet to prevent movement of the second arm along the crossbar in the first direction; and
    wherein the switch, when in a third position, configures the bidirectional ratchet to prevent movement of the second arm along the crossbar in both the first direction and the second direction.

2. The distractor of claim 1, wherein the distal end of the second arm comprises a lock configured to receive an upper portion of the second distraction screw and engage a locking groove in the upper portion of the second distraction screw.

3. The distractor of claim 1, wherein the bidirectional ratchet comprises:
    a first pawl;
    a second pawl;
    a first spring that biases the first pawl toward the teeth of the crossbar; and
    a second spring that biases the second pawl toward the teeth of the crossbar;
    wherein the switch comprises a longitudinal rod that passes through a first aperture in the first pawl and a second aperture in the second pawl;
    wherein the longitudinal rod comprises a first end portion, a second end portion, and a tapered portion between the first end portion and the second end portion;
    wherein the first end portion, the second end portion, and the tapered portion are sized such that the tapered portion aligns with the first pawl and the second end portion aligns with the second pawl when the longitudinal rod is slid through the first and second apertures to the first switch position;
    wherein the tapered portion permits the first spring to bias the first pawl against the teeth of the crossbar when in the first switch position; and
    wherein the second end portion moves the second pawl away from the teeth of the crossbar when in the first switch position.

4. The distractor of claim 1, wherein:
    the bidirectional ratchet further comprises a pinion having teeth that engage the teeth of the crossbar; and
    the bidirectional ratchet is configured to traverse the crossbar in response to rotation of the pinion.

5. The distractor of claim 1, wherein the second arm comprises a plurality of pivotally coupled portions.

6. A distractor for use with a first distraction screw and a second distraction screw, the distractor comprising:
    a crossbar comprising teeth;
    a first arm comprising a proximal end coupled to the crossbar and a distal end configured to receive the first distraction screw;
    a second arm comprising a proximal end coupled to the crossbar via a bidirectional ratchet and a distal end configured to receive the second distraction screw;
    wherein the bidirectional ratchet comprises:
        a first pawl;
        a second pawl;
        a first spring that biases the first pawl toward the teeth of the crossbar;
        a second spring that biases the second pawl toward the teeth of the crossbar; and
        a switch configured to selectively control ratcheted movement of the second arm along the crossbar;
    wherein the switch, when in a first switch position, configures the bidirectional ratchet to permit movement of the second arm along the crossbar in a first direction toward the first arm and configures the bidirectional ratchet to prevent movement of the second arm along the crossbar in a second direction away from the first arm;

wherein the switch, when in a second switch position, configures the bidirectional ratchet to permit movement of the second arm along the crossbar in the second direction and configures the bidirectional ratchet to prevent movement of the second arm along the crossbar in the first direction; and wherein the switch, when in the first switch position, is configured to move the second pawl away from the teeth of the crossbar and permit the first spring to bias the first pawl against the teeth of the crossbar.

7. The distractor of claim 6, wherein the first pawl comprises a first finger having a first edge that permits movement of the second arm along the crossbar in the first direction and a second edge that prevents movement of the second arm along the crossbar in the second direction, wherein the second edge has a steeper slope than the first edge.

8. The distractor of claim 6, wherein:
the switch, when in the second switch position, is configured to move the first pawl away from the teeth of the crossbar and permit the second spring to bias the second pawl against the teeth of the crossbar.

9. The distractor of claim 8, wherein the second pawl comprises a second finger having a first edge that permits movement of the second arm along the crossbar in the second direction and a second edge that prevents movement of the second arm along the crossbar in the first direction, wherein the second edge has a steeper slope than the first edge.

10. The distractor of claim 6, wherein the distal end of the second arm comprises a lock configured to receive an upper portion of the second distraction screw and engage a locking groove in the upper portion of the second distraction screw.

11. The distractor of claim 6, wherein:
the bidirectional ratchet further comprises a pinion having teeth that engage the teeth of the crossbar; and
the bidirectional ratchet is configured to traverse the crossbar in response to rotation of the pinion.

12. The distractor of claim 6, wherein the first arm comprises a plurality of pivotally coupled portions.

13. A distractor system, comprising:
a first distraction screw comprising a proximal end and a distal end having threads that affix first distraction screw to bone;
a second distraction screw comprising a proximal end and a distal end having threads that affix second distraction screw to bone;
a crossbar comprising teeth;
a first arm comprising a proximal end coupled to the crossbar via a first ratchet and a distal end configured to receive the proximal end of the first distraction screw;
a second arm comprising a proximal end coupled to the crossbar via a second ratchet and a distal end configured to receive the proximal end of the second distraction screw:
wherein the first ratchet comprises a first switch configured to select between ratcheted movement of the first arm along the crossbar toward the second arm and ratcheted movement of the first arm along the crossbar away from the second arm; and
wherein the second ratchet comprises a second switch configured to select between ratcheted movement of the second arm along the crossbar toward the first arm and ratcheted movement of the second arm along the crossbar away from the first arm, wherein the first switch, when in a first switch position, configures the first ratchet to permit movement of the first arm along the crossbar in a compression direction toward the second arm and configures the first ratchet to prevent movement of the first arm along the crossbar in a distraction direction away from the first arm;

wherein the first switch, when in a second switch position, configures the first ratchet to permit movement of the first arm along the crossbar in the distraction direction and configures the first ratchet to prevent movement of the first arm along the crossbar in the compression direction; and wherein the first switch, when in a third position, configures the first ratchet to prevent movement of the first arm along the crossbar in both the distraction direction and the compression direction.

14. The distractor system of claim 13, wherein the distal end of the first arm comprises a sleeve configured to receive the first distraction screw and a lock configured to engage a locking groove in the proximal end of the first distraction screw.

15. The distractor system of claim 13, wherein the first ratchet comprises:
a first pawl;
a second pawl;
a first spring that biases the first pawl toward the teeth of the crossbar; and
a second spring that biases the second pawl toward the teeth of the crossbar;
wherein the first switch, when in the first switch position, is configured to move the second pawl away from the teeth of the crossbar and permit the first spring to bias the first pawl against the teeth of the crossbar.

16. The distractor system of claim 15, wherein the first pawl comprises a first finger having a first edge that permits movement of the first arm along the crossbar toward the second arm and a second edge that prevents movement of the first arm along the crossbar away from the second arm, wherein the second edge has a steeper slope than the first edge.

17. The distractor system of claim 16, wherein the second pawl comprises a second finger having a first edge that permits movement of the first arm along the crossbar away from the second arm and a second edge that prevents movement of the first arm along the crossbar toward the second arm, wherein the second edge of the second finger has a steeper slope than the first edge of the second finger.

18. The distractor system of claim 13, wherein the first ratchet comprises:
a first pawl;
a second pawl;
a first spring that biases the first pawl toward the teeth of the crossbar; and
a second spring that biases the second pawl toward the teeth of the crossbar;
wherein the first switch comprises a longitudinal rod that passes through a first aperture in the first pawl and a second aperture in the second pawl;
wherein the longitudinal rod comprises a first end portion, a second end portion, and a tapered portion between the first end portion and the second end portion;
wherein the first end portion, the second end portion, and the tapered portion are sized such that the tapered portion aligns with the first pawl and the second end portion aligns with the second pawl when the longitudinal rod is slid through the first and second apertures to the first switch position;

wherein the tapered portion permits the first spring to bias the first pawl against the teeth of the crossbar when in the first switch position; and wherein the second end portion moves the second pawl away from the teeth of the crossbar when in the first switch position.

19. The distractor system of claim 13, wherein:

the first ratchet further comprises a pinion having teeth that engage the teeth of the crossbar; and the first ratchet is configured to traverse the crossbar in response to rotation of the pinion.

20. The distractor system of claim 13, wherein the first arm comprises a plurality of pivotally coupled portions.

* * * * *